United States Patent [19]
Uhl et al.

[11] Patent Number: 4,881,534
[45] Date of Patent: Nov. 21, 1989

[54] CORTICOTOMO OSTEOTOME WITH T-SHAPED CUTTING END

[76] Inventors: Richard L. Uhl, 36 Hawthorne Pl., Montclair, N.J. 07042; Robert J. Uhl, 29 Lake Dr., E., Wayne, N.J. 07470

[21] Appl. No.: 252,666

[22] Filed: Oct. 3, 1988

[51] Int. Cl.⁴ .............................................. A61B 17/32
[52] U.S. Cl. ........................................ 606/84; 606/79
[58] Field of Search ................. 128/305, 92 V, 92 VJ; 30/92.5, 168, 167.1, 167

[56] References Cited

U.S. PATENT DOCUMENTS

| | | | |
|---|---|---|---|
| 1,598,458 | 8/1926 | Sullivan | 30/168 X |
| 2,203,158 | 6/1940 | Klein | 30/92.5 |
| 2,465,305 | 3/1949 | Cope | 30/92.5 |
| 4,239,045 | 12/1980 | Schlein | 128/305 |

FOREIGN PATENT DOCUMENTS

| | | | |
|---|---|---|---|
| 1181640 | 9/1985 | U.S.S.R. | 128/305 |
| 1360711 | 12/1987 | U.S.S.R. | 128/92 V |

*Primary Examiner*—Michael H. Thaler
*Attorney, Agent, or Firm*—Howard E. Thompson, Jr.

[57] ABSTRACT

A corticotomy osteotome is provided comprising an elongated body having a cutting end and an anvil end adapted for engagement with a mallet in advancing the cutting end, wherein the cutting end is of T-shaped cross-sectional form with the cross head of the T providing bearing surfaces for engaging outer surfaces of the bone cortex, and a rib extending perpendicularly and centrally of the bearing surfaces which protrudes from the bearing surfaces a distance approximately equivalent to the thickness of the bone cortex, the rib terminating in a tapered cutting edge extending perpendicularly to the bearing surfaces and being spaced inwardly from the leading edge of such bearing surfaces, and the upper surfaces of the body being smoothly rounded and tapered in the direction of the leading edge of the bearing surfaces permitting the leading edge to lift the periosteum from the bone cortex and support it in spaced relation to the cortex as the osteotome is advanced to cut the cortex, and the anvil end being engagable by a transverse member facilitating axial twisting of the osteotome at the end of a cortex cutting operation to facilitate enlargement of the cut made in the cortex.

6 Claims, 2 Drawing Sheets

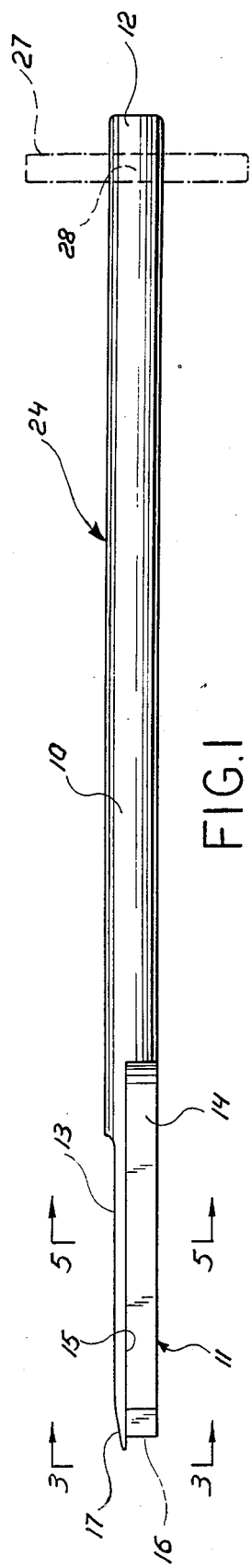
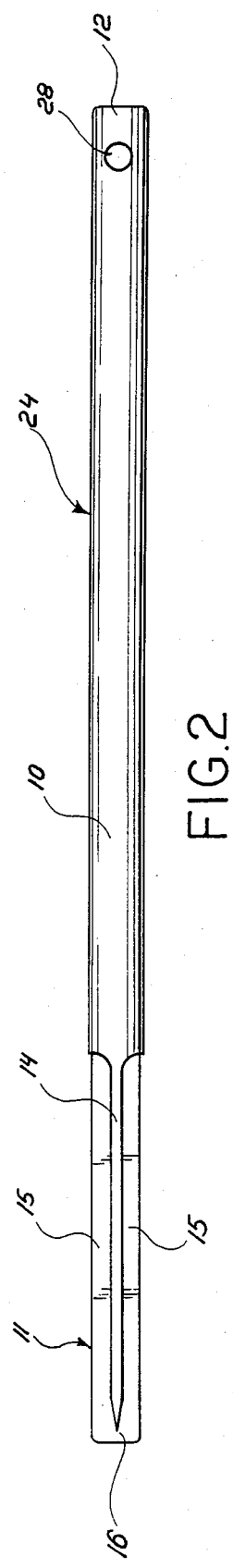
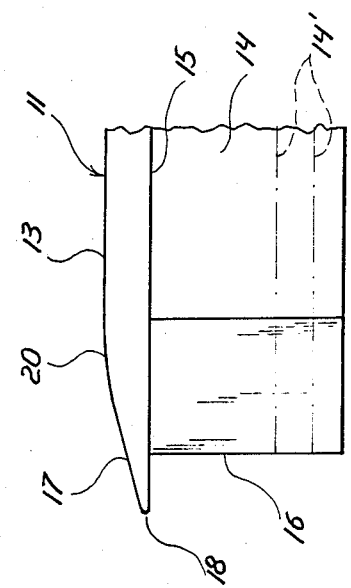
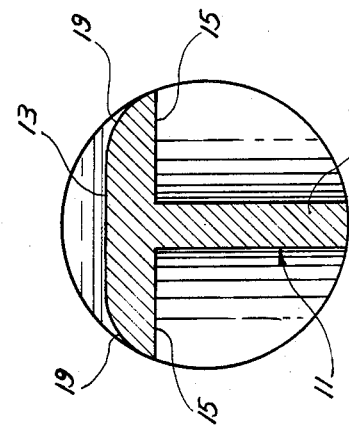
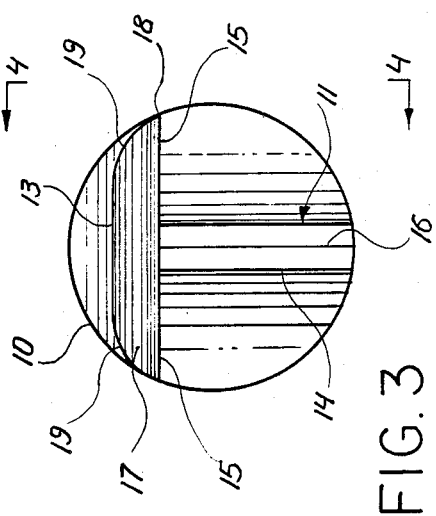

CORTICOTOMO OSTEOTOME WITH T-SHAPED CUTTING END

This invention relates to an improved corticotomy osteotome with a T-shaped cutting end which is adapted and intended for use in the Ilizarov techniques of limb lengthening and/or bone transport without bone grafting of the distraction gap.

BACKGROUND OF THE INVENTION

In about 1951 Dr. Gavriil A. Ilizarov of the Soviet Union developed a technique and supportive equipment for effecting limb lengthening which involves the circumferential severance of the cortex of a bone to be lengthened while minimizing damage to the periosteum and the medullary cavity, and then very gradually separating the severed cortex ends as new bone is generated in the distraction gap. The technique is useful both in the lengthening of initially sound bones in cases of dwarfism and in restoring original bone lengths in which there has been loss of bone through accident of disease.

Since originally developed the technique has been successfully used in about a million cases world-wide although the technique has only quite recently been introduced in the United States.

The supportive equipment, known as the Ilizarov External Fixator, comprises a plurality of rings arranged circumferentially of the limb to be lengthened which are adjustably assembled at appropriate positions longitudinally of the limb to support pins passing through portions of the limb for which relative movement is desired. There are other similar systems on the market as well.

The apparatus can be thought of as a Compression-Distraction Apparatus denoting its capability of both moving bony ends together as needed while at the same time accomplishing distraction at the location of annular severance or corticotomy of the bone cortex in the area where lengthening is desired.

This equipment is distributed in the United States by Richards Medical Company of Memphis, Tenn.; and its nature and use is extensively described and illustrated in a general surgical technique brochure entitled "The Ilizarov External Fixator" which is published and distributed by Richards Medical Company.

The equipment and technique is also extensively discussed in a review article entitled "Current Techniques in Limb Lengthening" by Dror Paley, M.D., F.R.C.S., (C) which appeared in the Journal of Pediatric Orthopedics 8:73-92 (1988).

As there described the Ilizarov technique involves initiation of distraction about seven days following corticotomy at the rate of about 1 mm per day suitably by making 0.25 mm adjustments in the Ilizarov External Fixator four times a day. This distraction rate may be increased or decreased slightly depending on the individual being treated; the important thing being that the distraction rate substantially coincide with the regeneration of cortex, and that it be fast enough to prevent consolidation of regenerated cortex which would prevent further distraction. With the distraction rate properly regulated a bone extension of as much as 6–8 inches can be accomplished by this technique.

The corticotomy according to the Ilizarov technique is accomplished as follows:

(1) Make a 1 cm longitudinal incision just lateral to the tibial crest. Cut down to and through periosteum. Insert a periosteal elevator medially and laterally to elevate the periosteum at the level of the bone cut. Insert a 1 cm osteotome into the rent in the periosteum and turn the osteotome 90 degrees, (2) Cut into the anterior cortex of the tibia, creating a groove with the osteotome.

(3) The cut should extend to but not through the medullary cavity.

(4) Remove the 1 cm osteotome and carefully insert a periosteal elevator on the lateral side, thus stripping the periosteum and lifting it from the bone. The elevator should reach around the posterolateral cortex. With the elevator lying flat against the bone, the direction of the cut can be appreciated.

(5) Insert a 5 mm osteotome under the protection of the elevator. Cut the cortex down to and through the posterolateral corner. Keep the osteotome in the cortex only. Do not penetrate deeply into the medullary cavity. Do not slide out of the cortex inadvertently. Remove the osteotome by slightly twisting it side to side to loosen it in the bone rather than using a window wiper maneuver which may damage the medullary cavity.

(6) Repeat the same maneuver on the medial side. Cut to and through the posteromedial cortex.

(7) Twist the osteotome, which is located in the posteromedial corner, 90 degrees. This will spread the osteotomy apart like a laminar spreader and begin the osteoclasis of the posterior cortex.

(8) Repeat the same maneuver on the medial side. This should complete the fracture of the posterior cortex. This maneuver may need to be repeated several times on the medial and lateral side until one is convinced that the posterior cortex is broken. Once these maneuvers are completed, rotate the distal ring externally, relative to the proximal ring. This will avoid stretching the peroneal nerve and will complete and ensure the osteoclasis.

In the technique as above described the use of a conventional flat osteotome of 5 mm or other appropriate width in the circumferential cutting of cortex is a delicate operation requiring great care and skill if inadvertent damage to the periosteum or the meduallary cavity is to be prevented. Damage in these areas, and particularly damage to the medullay cavity and the nutrient arteries can complicate and greatly prolong the bone regeneration and the progress of a desired distraction.

THE INVENTION

The improved osteotome of the present invention overcomes this difficulty and makes it vastly easier for surgeons to become proficient in the Ilizarov technique. In the improved osteotome the cutting end is provided with a T-shaped cross sectional configuration with the cross-head of the T providing bearing surfaces for engaging the outer surface of the bone cortex with the perpendicularly disposed rib being of a height or depth which is approximately equivalent to the thickness of the bone cortex. The leading end of the rib is provided with a tapered and sharpened cutting edge perpendicular to the bearing surfaces and slightly inwardly spaced from the leading edge thereof.

The upper surface of the cross head of the T-shaped configuration is smoothly rounded and tapered toward the leading edge thereof, with such leading edge being a rounded, non-cutting edge thereby facilitating lifting of the periosteum from the cortex and supporting the same spaced from the cortex as the cutting edge of the rib is advanced circumferentially of the bone cortex. Such advancing of the cutting edge is accomplished by tapping the remote, anvil end of the osteotime with a mallet; and in thus advancing the cutting edge, with the bearing surfaces held tightly against the bone cortex, there should be little, if any, damage to either the periosteum or the meduallary cavity.

The anvil end of the osteotome is provided with laterally extending means, such as a pin extending through a transverse aperture therein, to permit axial rotation of the osteotome both for freeing the osteotome from the cut which has been made and for stressing the cortex to extend fracture beyond the end of the cut. The latter type of operation comes into play particularly after circumferential cuts have been made along two sides of a bone and it becomes necessary to extend the cuts to accomplish a full fracture at the posterior side of the bone. Because the T-shaped configuration of the cutting end of the osteotome limits the extent of axial rotation which is practical, it may be difficult with the T-shaped osteotome along to complete full fracture of the posterior portion of the bone.

In such event it is appropriate, along each of the cortex cuts which have been made, to insert a periosteal elevator and then to carefully insert a conventional flat osteotome of appropriate width in the cut which has been made in the cortex. This flat osteotome can be axially rotated a full 90 degrees thereby facilitating the application of force needed to complete fracture of the posterior portion of the bone cortex. To minimize the chance of damage to the periosteum or meduallary cavity in this procedure the flat osteotome is suitably modified by dulling the cutting edge and rounding the corners thereof.

This procedure, using the conventional or modified flat osteotome, should be repeated in the cortex cuts made along both sides of the bone until the extension of fracture beyond such cuts has completed severance of the posterior bone cortex.

It will be noted in this connection that the engagement of the bone above and below the site of the corticotomy by components of the Ilizarov External Fixator serves to maintain the bone parts in proper alignment as severance of the cortex is completed; and confirmation of completion of the cortex severance can be accomplished by slight relative rotation of the External Fixator components.

The improved osteotome of the present invention not only enhances the safety of the Ilizarov technique for those already skilled in the technique, but also makes it possible for any orthopedic surgeon to rapidly develop skills in the technique.

The improved osteotome with cutting end of T-shaped configuration is believed to be distinctly new and patentable. A search in the United States Patent Office has developed no prior art considered to have a direct or anticipatory bearing on this improved construction. The following four patents, all exceedingly remote, are cited as generally illustrative of the art:

U.S. Pat. No. 2,203,158 issued June 4, 1940 relating to "Chisel for removing boiler tubes" has a cutting end of generally T-shaped configuration, but the cross head of the T is tapered on the under side for lifting a boiler tube wall into the path of a vertically disposed blade, a function directly opposed to the function of the improved osteotome of the present invention.

U.S. Pat. No.1,114,903 issued Oct. 27, 1914 relates to a reefing iron which is a device for cleaning out seams of wooden ships preparatory to caulking such ship seams. It provides a T-shaped configuration for controlling the depth of cut with the forward end of transverse bearing surfaces being divided to permit lifting of debris cut from a seam by an angularly disposed blade.

U.S. Pat. No. 2,465,305 issued Mar. 22, 1949 relating to "Cutting Instrument" is intended for breaking telescoped piping Joints. It provides a cutting end of generally T-shaped configuration with a cross head of the T being tapered on the inner side thereof to permit necessary insertion between inner and outer telescoping pipes to permit cutting of the outer pipe.

U.S. Pat. No. 4,600,005 dated July 15, 1986 relates to "Guided Osteotome for Harvesting Cranial Bone Graft". This device is a relatively wide chisel for removing thin layers of cranial bone and is significant only in providing laterally extending means for bearing against bone surface to limit the depth of cut.

There is nothing in these patents, whether considered separately or in combination, to suggest the unique construction of the present invention in which the T-shaped configuration of an osteotome cutting end provides control of the depth of cortex cut while lifting and protecting the periosteum in advancing of the cortex cutting edge.

The improved osteotome in accordance with present invention and its manner of use will be more fully understood from a consideration of the accompanying drawings in which various parts of the device and components with which it is used are identified by suitable reference characters in the several views, and in which:

FIG. 1 is a side elevation view of the improved osteotome.

FIG. 2 is a bottom view of the improved osteotome.

FIG. 3 is an end view of the device taken in the direction of the arrows 3—3 in FIG. 1.

FIG. 4 is an enlarged view of the end structure shown in FIG. 4.

FIG. 5 is a sectional view taken substantially on the line 5—5 of FIG. 1; and

Figure 6:
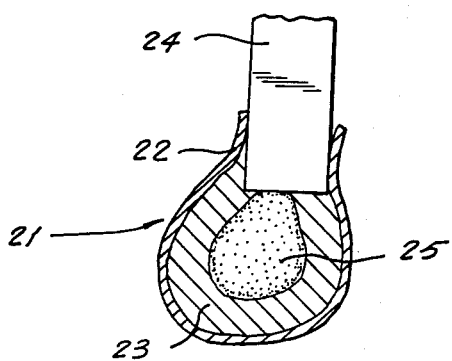
FIGS. 6 to 11 are illustrations of sequential steps in accomplishing a corticotomy using the improved osteotome in association with conventional surgical instruments.

As shown in FIGS. 1 to 5 the improved osteotome 24 comprises an elongated body 10 having a cutting end 11 and an anvil end 12 intended to be tapped with a mallet in the use of the device. The body 10 is shown as being of cylindrical cross-section suitably about 0.375" in diameter, with stainless tool steel being a preferred starting material. It should be understood, however, that the device can be made in various sizes, and that the cross section of the body portion can be varied as desired.

In fashioning the cutting end 11, one side of the cylindrical body 10 is milled for a distance of about 2.5" to provide a flattened surface 13; and opposed sides of the body 10 are milled, in planes perpendicular to the first milling, and extending about 2.75" along the body 10, to provide bearing surface 15 approximately 0.06" below the flattened surface 13, with the thickness of the rib 14 also being approximately 0.06". These millings provide a general T-shaped contour to the cutting end 11 as clearly shown in FIGS. 3 and 5 of the drawing.

The end of the rib 14 is then milled to form a cutting end 16 terminating about 0.08" short of the ends of the bearing surfaces 15 with said cutting edge suitably having approximately a 20" taper.

The end portion is then milled for a distance of about 0.12" at a downward incline with respect to surface 13 as shown at 17 with the intersection of this inclined surface and bearing surfaces 15 being rounded as seen at 18. This provides a "non-cutting" leading edge for separating the periosteum from the cortex in the use of the device.

As shown in FIGS. 3 to 5 upper surfaces of the T-shaped cutting end are smoothly rounded along peripheral edges of the surface 13 as seen at 19 and 20 to permit these surfaces to freely slide under the lifted periosteum.

The height of the cutting rib 14, as originally fashioned from drill steel of the size described will be about 0.256". It should be noted that this height should correspond quite closely with the thickness of the cortex of the bone in which the corticotomy is being performed; and the rib height described would be appropriate for use on relatively large bones. It will be understood, however, that the device should be provided in several sizes differing in height of the rib 14, with typical variations being indicated by the dotted lines 14' shown in FIG. 4 of the drawing.

The ideal size for any particular corticotomy would be the instrument having a rib height sufficient to go through the cortex without significant penetration into the medullary cavity. In this connection it is to be understood that the various dimensions specified above can be proportionally increased or decreased in providing different size devices to accommodate variations in bone size and cortex thickness. Incidentally, cortex thickness may be approximated by X-ray determination.

To visualize how the T-osteotome of the present invention is utilized attention is directed to FIGS. 6 to 11 of the drawing. The initial steps are identical to those of Ilizarov as described in the earlier mentioned Paley publication. A 1 cm incision is made longitudinally of the bone 21, extending through the periosteum 22 and to the bone cortex 23. A 1 cm osteotome of standard flat construction 24 is inserted in this incision, twisted perpendicularly to the bone axis and tapped with a mallet to penetrate the bone cortex 23, as shown in FIG. 6 without significantly entering the medullary cavity 25.

Figure 7:
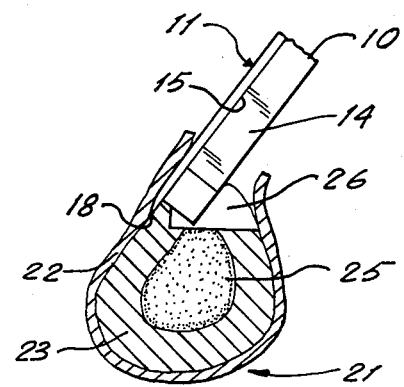
Figure 8:
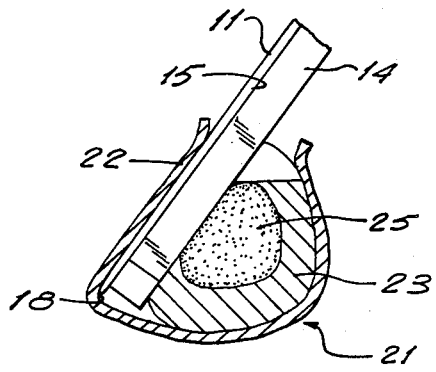

After removal of the osteotome 24 the cutting end 11 of the T-osteotome 24 of the present invention is inserted in the cortex cut 26 with the leading edge 18 under the periosteum 22 and surfaces 15, bearing against the outer surface of the cortex 23, as shown in FIG. 7. Then, while holding the bearing surface 15 closely against the bone cortex 23, the T-osteotome is advanced by tapping the anvil end 12 with a mallet to progressively lift the periosteum 22 and cut through the cortex 23 until reaching the position shown in FIG. 8. Then, with the assistance of a rod 27, inserted in aperture 28 in the anvil end 12 of the T-osteotome, the device is axially twisted to enlarge the cut and permit its free removal.

Figure 9:
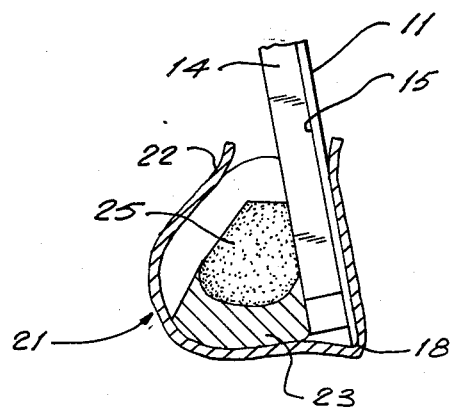
Figure 10:
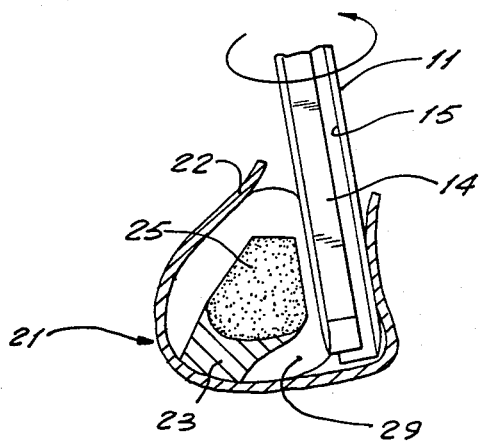

The steps just described are repeated on the other side of the bone as illustrated in FIG. 9; and with the completion of this second cutting of the bone cortex the T-osteotome is subjected to more strenuous axial twisting to initiate cracking of the cortex beyond the cut as seen at 29 in FIG. 10.

Figure 11:
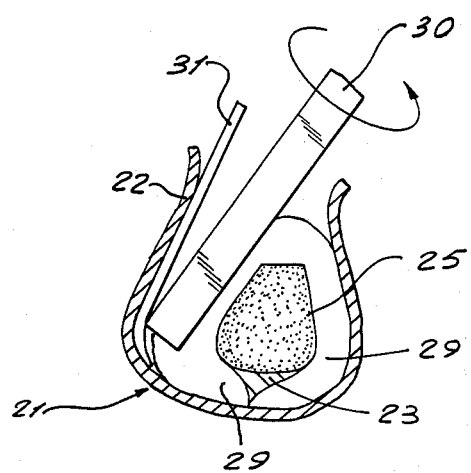

After removing the T-osteotome the final breaking of the bone cortex 23 is accomplished as shown in FIG. 11 by means of a conventional flat osteotome 30 which is inserted and axially twisted as shown. To prevent damage to the periosteum it is preferable to first insert a periosteal elevator 31 extending to a point beyond the end of the osteotome 30, and/or to use a flat osteotome which has been modified to have a dulled cutting edge and rounded corners. The illustration in FIG. 11 shows a small section of cortex 23 still unruptured; and suitably the insertion and twisting of the flat osteotome 30 is repeated at opposite sides of the bone until complete annular separation of the bone cortex has been accomplished.

In the procedure as above described it will be apparent that the periosteum has been protected from significant damage and there has been very little entry into the medullary cavity, while a complete annular break in the bone cortex has been accomplished. Thus the stage has been set for efficient and uncomplicated bone lengthening according to the Ilizarov technique. The use of the T-osteotome has been of special advantage in preventing inadvertent and harmful penetration of the medullary cavity, in both cadaver and in actual surgically performed corticotomies.

Various changes and modifications in the T-osteotome as herein described may occur to those skilled in the art, and to the extent that such changes and modifications are embraced by the appended claims, it is to be understood that they constitute part of the present invention.

We claim:

1. A corticotomy osteotome comprising an elongated body having a cutting end an an anvil end adapted for engagement with a mallet in advancing the cutting end, wherein the cutting end is of T-shaped cross-sectional form with the cross-head of the T providing closely spaced and essentially parallel inner and outer bearing surfaces for engaging respectively the outer surface of the cortex, and the inner surface of the periosteum, and a rib extending perpendicularly and centrally of the inner bearing surface a distance approximately equivalent to the thickness of the bone cortex, the rib having closely spaced parallel surfaces terminating in a tapered cutting edge extending perpendicularly to said inner bearing surface, and being spaced inwardly from the leading edge of said inner bearing surface, and the outer bearing surface being smoothly rounded along its edges and tapered in the direction of said leading edge of the inner bearing surface permitting the leading edge to lift the periosteum from the bone cortex, and support it in spaced relation to the cortex, as the osteotome is advanced to cut the cortex, and the anvil end having means engagable by a transverse member providing leverage for axial twisting of the osteotome at the end of a cortex cutting operation to facilitate enlargement of the cut made in the cortex.

2. A corticotomy osteotome as defined in claim 1, wherein the T-shaped cutting end is characterized in that the T cross-head and the protruding rib have a similar thickness of approximately 0.06".

3. A corticoticotomy osteotome as defined in claim 1, wherein the T-shaped cutting end is characterized in that the T cross-head and the protruding rib have a similar thickness of approximately 0.06", and the cutting edge of the rib is about 0.08" inwardly of the leading edge of the bearing surfaces.

4. A corticotomy osteotome as defined in claim 1, wherein the outer bearing surface taper of the cutting end extends about 0.12" from the leading edge of the bearing surfaces, and terminates in a smoothly rounded, non-cutting leading edge.

5. A corticotomy osteotome as defined in claim 1, wherein the elongated body is cylindrical drill-steel approximately 0.375" in diameter, and the T-shaped configuration of the cutting end is provided by removing portions of said cylindrical body.

6. A corticotomy osteotome as defined in claim 5, wherein the means engagable by a transverse member is a transaxial aperture in the anvil end for slidably receiving a pin, said aperture being aligned with the rib of said cutting end.

* * * * *